United States Patent [19]

Petrov et al.

[11] Patent Number: 5,457,238

[45] Date of Patent: Oct. 10, 1995

[54] PROCESS FOR THE PREPARATION OF FLUOROKETONES

[75] Inventors: Viacheslav A. Petrov; Bruce E. Smart, both of Wilmington, Del.

[73] Assignee: E. I. Du Pont de Nemours and Company, Wilmington, Del.

[21] Appl. No.: 268,393

[22] Filed: Jun. 30, 1994

[51] Int. Cl.[6] ................................... C07C 45/70
[52] U.S. Cl. .................... 568/384; 558/440; 568/310
[58] Field of Search .................... 568/310, 419, 568/384, 380; 558/440

[56] References Cited

U.S. PATENT DOCUMENTS

| | | | |
|---|---|---|---|
| 3,213,134 | 10/1965 | Morin | 260/544 |
| 3,321,515 | 5/1967 | Moore et al. | 260/544 |
| 4,238,416 | 12/1980 | Tohzuka et al. | 568/384 |
| 4,302,608 | 11/1981 | Squire | 568/384 |
| 4,400,546 | 8/1983 | Rammelt et al. | 568/384 |

FOREIGN PATENT DOCUMENTS

| | | | |
|---|---|---|---|
| 58-62130 | 4/1983 | Japan | 568/384 |

OTHER PUBLICATIONS

Knunyants, I. L. et al., "Perfluoropropylene Oxide in Reactions with Electrophilic Reagents", translated from *Izvestiya Akademiii Nauk SSSR, Seriya Khimicheskaya*, 12, 2725–2730, Dec. 1973 (Institute of Heteroorganic Compounds, Academy of Sciences of the USSR). CA 80, 95151 (1974).

Zapevalov, A. Ya et al., "Syntheses and Reactions of Oxygen–Containing Organofluorine Compounds. II. Catalytic and Thermal Transformations of 6H–Undecafluoro–1, 2–epoxyhexane", translated from *Zhurnal Organicheskoi Khimii*, 11(8), 1622–1625, Aug. 1975. (Institute of Chemistry, Ural Scientific Center, Academy of Sciences of the USSR) CA 83, 192954 (1975).

Zapevalov, A. Ya. et al., "Isomeric Transformations of Internal Perfluorinated α–Oxides", translated from *Zhurnal Organicheskoi Khimii*, 22(1), 93–99, Jan. 1986. (Institute of Chemistry, Urals Scientific Center. Academy of Sciences of the USSR) CA 106,4771.

Filyakova, T. I. et al., "Synthesis of Oxygen Containing Organofluorine Compounds and Their Reactions XI. Liquid Phase Oxidation of Perfluoro–1,5–Hexaidene by Atmospheric Oxygen", translated from *Zhurnal Organicheskoi Khimii*, 27(10), 2055–2060, Oct. 1991. (Institute of Chemistry, Bashkir Scientific Center, Urals Branch, Russian Academy of Sciences, Sverdlovsk.

Saloutina, L. A. et al., "Synthesis of Polyfluorochloro Ketones", translated from *Izvestiya Akademii Nauk SSSR, Seriya Khimicheskaya*, 6, 1434–1437, Jun. 1983. (Institute of Chemistry, Ural Scientific Center, Academy of Sciences of the USSR, Sverdlovsk). CA 99, 157790 z, 1983.

*Primary Examiner*—James H. Reamer

[57] ABSTRACT

This invention concerns a process for the preparation of fluoroketones by the isomerization of corresponding epoxides, in the presence of an aluminum chlorofluoride catalyst. Fluorinated ketones are useful intermediates for the synthesis of various fluorinated compounds.

10 Claims, No Drawings

PROCESS FOR THE PREPARATION OF FLUOROKETONES

FIELD OF THE INVENTION

This invention concerns a process for the preparation of fluoroketones by the isomerization of the corresponding epoxides in the presence of a Lewis acid catalyst. Fluorinated ketones, such as hexafluoroacetone, are useful intermediates for the synthesis of a variety of fluorinated compounds.

TECHNICAL BACKGROUND

U.S. Pat. No. 4,302,608 discloses a continuous process for isomerisation of hexafloropropylene oxide (HFPO) to hexafluoroacetone in the presence of an antimony pentafluoride ($SbF_5$) catalyst.

U.S. Pat. No. 3,213,134 discloses the isomerization of epoxide of perfluoroheptene-1 into perfluoroheptanone-2.

U.S. Pat. No. 3,321,515 teaches that HFPO can be converted into hexafluoroacetone (HFA) by reaction with alumina at 100° C. (yield 47%) or by reaction with $AlCl_3$.

I. L. Knunyants, V. V. Shokina and E. I. Mysov in Izv. AN SSSR. Ser. Khim. 2725 (1973) CA 80, 95151 (1974) disclose the reaction of HFPO with $SbCl_5$ at 170° C. to give a mixture of 15% of chloropentafluoroacetone and 80% of HFA.

A. Ya. Zapevalov, I. P. Kolenko, V. S. Plashkin Zh. Org. Khim. 11,1622 (1975), CA 83, 192954 (1975), and A. Ya. Zapevalov, T. I. Filyakova, M. I. Kodess, I. P. Kolenko Zh. Org. Khim. 22 (1), 93–9 (1986), CA 106, 4771 disclose the use of $SbF_5$ as catalyst for the isomerization of a number of higher epoxides of polyfluoroolefines but all their examples are limited to fluoroolefins without functional groups because of incompatability of $SbF_5$ with such groups, for example as —C(O)F. See: T. I. Filyakova, R. E. Ilatovskii, A. Ya. Zapevalov Zh. Org. Khim. 27, No10, 2055–60 (1991).

Aluminum chloride has limited use in ring-opening reaction of fluoroepoxides because of extensive formation of by-products. See L. A. Saloutina, A. Ya. Zapevalov, M. I. Kodess, I. P. Kolenko and L. S. German Izv. AN SSSR. Ser. Khim. 1434 (1983), CA 99, 157790 z, 1983.

Use of the present process with its aluminum chlorofluoride Lewis acid catalysts improves upon the processes and catalysts dislosed in the art by allowing for better yields with less by-product formation under generally milder temperature and pressure conditions.

SUMMARY OF THE INVENTION

This invention provides a process for the preparation of fluoroketones of the structure:

$R_fCF_2C(O)CFXY$ wherein X is F or Cl and Y is selected from the group consisting of F, Cl, and $R_f$, wherein $R_f$ is F or $C_1$–$C_5$ fluoroalkyl, said $C_1$–$C_5$ fluoroalkyl optionally containing in-chain oxygen and terminal functional groups; by isomerization of fluorinated epoxides of terminal and internal olefins in the presence of an aluminum chlorofluoride Lewis acid catalyst selected from aluminum chlorofluoride $AlF_nCl_{3-n}$, wherein n is from 0.05–2.95.

The process can be carried out in the optional presence of one or a mixture of inert solvents.

Use of a solid aluminum mixed halide catalyst avoids the handling problems experienced with, for example, $SbF_5$, which is a viscous, corrosive liquid.

DETAILED DESCRIPTION OF THE INVENTION

Polyfluorinated ketones $R_fCF_2C(O)CFXY$ are prepared by the isomerization of epoxides in the presence of a Lewis acid catalyst, such as $AlF_nCl_{3-n}$, wherein n is from 0.05 to 2.95, preferably 2.0 to 2.95. Epoxides useful herein are of the formula

$R_fCFOCFCFXY$ where X is F or Cl and Y is selected from the group consisting of F, Cl, and $R_f$, wherein $R_f$ is F or $C_1$–$C_5$ fluoroalkyl, said $C_1$–$C_5$ fluoroalkyl optionally containing in-chain oxygen and terminal functional groups such as —CN, —$OC_6F_5$, —C(O)R' (wherein R' is $C_1$–$C_5$ alkyl), —$SO_2F$, —C(O)F. The most preferred epoxide herein is hexafluoropropylene oxide (HFPO).

The reaction is carried out in the presence of an aluminum halide Lewis acid catalyst, wherein the aluminum halide is a mixed halide containing F and at least one of Cl, Br or I. Preferred catalysts are of the structure $AlF_nCl_{3-n}$ wherein n is from 0.05 to 2.95, preferably 2.0 to 2.95. Fluorinated aluminum chloride catalysts can be prepared by the reaction of $AlCl_3$ and $CFCl_3$, according to the method described in U.S. Pat. No. 5,162,594, column 4, lines 35–57, which is incorporated herein by reference. Catalyst may be preformed or may be generated in situ. Reactants and catalysts should be free of moisture.

The proportion of catalyst to epoxide is 0.05 to 0.2 mol catalyst per mole of epoxide.

Reaction temperature is about 0°–200° C. preferably about 20° C. to 100° C. Reaction times can vary from several seconds to about twenty four hours, depending upon temperature, catalyst activity and starting materials.

Solvents are generally not required for the reaction but may, optionally, be used if the solvents are relatively inert to the reaction conditions. By "relatively inert" herein is meant substantially unreactive toward the catalyst at reaction temperatures. Materials suitable for solvents herein are perfluoroalkanes, perfluorocycloalkanes, and perfluoroethers. In some cases, the ketone product of the process can be advantageously used as the solvent.

The process can be carried out in a batch or continuous mode. The reaction can be carried out in the gas phase, in a flow system over a fixed bed catalyst, such as the aluminum chlorofluoride catalyst.

The products of the process are useful intermediates for the synthesis of various fluorinated compounds. For example, HFA is used in the synthesis of bisphenol AF.

EXAMPLES

Catalyst preparation, 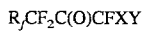

500 g (3.75 mol) of $AlCl_3$ (Aldrich-99% pure) was stirred mechanically under $N_2$ in a round bottom flask fitted with a −80° C. condenser while 1750 mL (about 2625 g, 19 mol) of $CFCl_3$ was added over a 1.5 hr period. Reaction is very exothermic in the early stages, so addition of $CFCl_3$ was slow at first in order to keep the temperature below 65° C., then rapid. The resulting suspension was stirred an additional 3 hrs while volatiles ($CF_2Cl_2$) were allowed to escape through the condenser. The condenser was then replaced with a simple stillhead, and most of the $CCl_4$ was distilled under reduced pressure [mainly bp 38° C. (200 mm)]. Finally, the last traces of volatiles were removed by warming the residual solid to 30°–35° C. at 0.05 mm Hg pressure.

The sealed round bottom flask was transferred to a dry box and unloaded into a Teflon® FEP bottle; 340 g of rather finely divided yellow-green solid was obtained. Portions of the catalyst were weighed out in the dry box as needed and taken out in plastic bottles with pressure-seal caps.

Analysis for fluorine of the products from preparation of this type indicated the composition to be $AlF_{2.9}Cl_{0.1}$, $AlF_nCl_{(3-n)}$; n=2.9. The aluminum chlorofluoride catalyst is abbreviated ACF herein.

EXAMPLE 1

Two g of ACF and 20 mmol of HFPO were loaded into an evacuated cylinder through a vacuum line at −196° C. The cylinder was warmed up to 25° C. After 2 h at this temperature, gas-phase IR confirmed that all HFPO was converted into HFA. The yield was quantitative.

EXAMPLE 2

Inside of a dry box, 0.3 g of ACF was placed in a 5 mL glass sample tube equipped with Teflon stopcock; 1 g of oxide

was added in one portion. The tube was closed. Exothermic reaction was observed. After 2 h only the corresponding ketone $CNCF_2CF_2OCF_2C(O)CF_3$ was found in the sample tube according to $^{19}F$ NMR, IR and GC. IR (neat): 2273 (CN), 1807 (C=O) cm$^{-1}$. The yield was quantitative.

EXAMPLE 3

As in Example 2, 0.3 g of ACF was used for quantitative isomerization of 1 g of oxide

into ketone $C_6F_5OCF_2 C(O) CF_3$. IR: 1802 (C=O) cm$^{-1}$, on the $^{19}F$ NMR spectrum corresponds to the proposed structure.

EXAMPLE 4

As in Example 1, a mixture of 0.5 g ACF and 5 g of perfluoro-2,3-epoxypentane (85% purity, the rest perfluoropentene-2) was kept at 150° C. for 18 h. According to GC and $^{19}F$ NMR data, the reaction mixture contained 37% perfluoro-2-pentanone, 26% perfluoro-3-pentanone, 22% of starting oxide and 15% of perfluoro-pentene-2. Conversion of oxide was 74%, yield of ketones >95%.

EXAMPLE 5

Hexafluoropropylene oxide (13.8 g) was bubbled through a suspension of 2 g of ACF suspended in 50 mL of the cyclic dimer of hexafluoropropene at the rate of 0.04 g/min at 25° C. and atmospheric pressure. The outcoming gases (19.3 g) were collected in a cold (−78° C.) trap protected against atmospheric moisture. The product, according to $^{19}F$ NMR data, was a mixture of 68% of hexafluoroacetone and 32% of solvent, no starting material was found. The yield of HFA was 94%, conversion of hexafluoropropylene oxide was 100%.

What is claimed is:

1. A process for the preparation of fluoroketones of the structure:

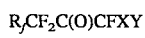

wherein X is F or Cl and Y is selected from the group consisting of F, Cl, and $R_f$, wherein $R_f$ is F or $C_1$–$C_5$ fluoroalkyl, said $C_1$–$C_5$ fluoroalkyl optionally containing in-chain oxygen and terminal functional groups comprising:

isomerization of fluorinated epoxides of terminal and internal olefins of the structure:

where X, Y and $R_f$ are as defined above, in the presence of a Lewis acid catalyst selected from the group consisting of aluminum chlorofluoride $AlF_nCl_{3-n}$, wherein n is from 0.05 to 2.95.

2. The process of claim 1 wherein n is 2.0 to 2.95.

3. The process of claim 1 carried out in the presence of an inert solvent.

4. The process of claim 3 wherein the solvent is selected from the group consisting of perfluoroalkanes, perfluorocycloalkanes, and perfluoroethers.

5. The process of claim 3 carried out in the fluoroketone product of claim 1.

6. The process of claim 1 carried out at a temperature of 0° C. to 200° C.

7. The process of claim 1 carried out at a temperature of 20° C. to 100° C.

8. The process of claim 1 wherein the proportion of catalyst to epoxide is 0.05 to 0.2 mole of catalyst per mole of epoxide.

9. The process of claim 1 carried out over a bed of solid catalyst.

10. The process of claim 1 wherein the starting material is HFPO and the product is HFA.

* * * * *